US005281017A

United States Patent [19]

Geiss, II

[11] Patent Number: 5,281,017

[45] Date of Patent: Jan. 25, 1994

[54] WHEELCHAIR ACCESSIBLE DESK/LIFT

[76] Inventor: Michael J. Geiss, II, 531 Oak St., Syracuse, N.Y. 13203

[21] Appl. No.: 888,146

[22] Filed: May 26, 1992

[51] Int. Cl.[5] ........................ A47B 17/02; A61B 19/02

[52] U.S. Cl. .................................... 312/194; 312/209; 312/319.8; 414/921: 414/541; 414/672

[58] Field of Search ............ 312/194, 209, 312, 319.5, 312/319.8; 414/921, 541, 672

[56] References Cited

U.S. PATENT DOCUMENTS

| | | | |
|---|---|---|---|
| 2,841,410 | 7/1958 | Kessler, Jr. et al. | 312/194 |
| 3,048,461 | 8/1962 | Peterson | 312/312 |
| 3,439,815 | 4/1969 | Wagner et al. | 414/672 |
| 4,095,859 | 6/1978 | Decker et al. | 312/209 |
| 4,249,785 | 2/1981 | Hapgood et al. | 312/196 |

FOREIGN PATENT DOCUMENTS

| | | | |
|---|---|---|---|
| 92/10422 | 6/1992 | World Int. Prop. O. | 414/921 |

OTHER PUBLICATIONS

"Sports Illustrated" article: Heightening Fan Enjoyment.

*Primary Examiner*—P. W. Echols
*Assistant Examiner*—David P. Bryant
*Attorney, Agent, or Firm*—Katherine McGuire

[57] ABSTRACT

A combination desk and wheelchair-lift adapted primarily for medical-surgical examination/treatment of a wheelchair-seated person comprises a mobile desk unit having a selectively retractable caster assembly. The wheelchair lift is attached to the desk by a linking slider assembly and is movable between a stored position underneath the desk and an extended position spaced from the desk. When in the extended position, a wheelchair may be rolled onto the wheelchair-lift rotatable platform and raised in a vertical direction by electrically actuated lifting mechanisms on either side of the platform. A clamp assembly is provided adjacent one of the lifting mechanisms for attaching a variety of diagnostic examination/treatment or medical-surgical equipment positioned adjacent the patient seated in the wheelchair.

17 Claims, 7 Drawing Sheets

WHEELCHAIR ACCESSIBLE DESK/LIFT

BACKGROUND OF THE INVENTION

This invention relates to ergonomic structures for the physically disabled and, more particularly, to a combined desk and wheelchair-lift assembly designed for professional examination/treatment of any person seated in a wheelchair. Further, the device is intended for use by a person seated in a wheelchair as a desk-/workstation.

For medical examination and/or treatment, it is preferable that a patient be seated in a customary examination/treatment chair. However, in the case of a wheelchair patient, it is not always possible or practical to unseat and move a patient from their wheelchair. In this case, the wheelchair with patient and professional equipment must be juxtapositioned. Since, for example, ophthalmic equipment is designed to service a patient seated in the specially designed examination chair, it proves awkward and clumsy when attempting to service a patient seated in a wheelchair. The position of a wheelchair-seated patient's head is much lower than the head of a patient seated in an examination/treatment chair. Procedures involving the patient's head require the use of certain equipment which must be positioned directly at the patient's head. As a result, professional caregivers have found that they must either bend uncomfortably or occasionally get on their knees to be at the needed examination height. Examination/treatment involving the lower extremities of wheelchair-seated patients are likewise inconvenient.

It is therefore a principle object of the present invention to provide an examination/treatment desk and wheelchair-lift combination which allows the professional a more convenient and comfortable working posture while, at the same time, providing an improved level of care to a person seated in a wheelchair.

It is another object of the present invention to provide an examination/treatment desk and wheelchair-lift combination which is mobile and of a size and configuration such that it may be easily transported and maneuvered into and through cramped spaces thereby increasing and facilitating accessibility to wheelchair-seated patients.

It is a further object of the present invention to provide a mobile desk and wheelchair-lift combination which may be used by wheelchair-seated people for a variety of purposes other than professional care, e.g., as a work desk at which they may position and adjust themselves with vertical, horizontal and rotational freedom.

It is yet another object of the present invention to provide a desk and wheelchair-lift combination which provides for quick and easy attachment and interchangeability of various medical and non-medical equipment thereto.

Other objects will in part be obvious and in part appear hereinafter.

SUMMARY OF THE INVENTION

In accordance with the foregoing objects, the invention comprises a novel and unique desk assembly with wheelchair-lift designed primarily for ophthalmic examinations of wheelchair-seated patients although many other uses are envisioned and within the province of the invention as will be more fully appreciated hereinafter.

The desk portion of the invention is of generally rectangular configuration and includes a handle and swivel casters making the unit mobile and easily maneuverable through doors, hallways and cramped spaces. Means are provided to selectively retract the casters to a non-mobile position within the legs of the desk such that the bottoms of the desk legs contact and rest directly and firmly upon the floor when the invention is in use.

A plurality of vertically stacked shelves ar hingedly connected to the top surface of the desk and may be swung from a first, closed position where the shelf unit lies flush and below the top surface of the desk, to a second, open position where the shelf unit sits upon the top surface of the desk whereupon it may be used to place needed specialty items. Such items might include projection and lighting equipment. In addition to the shelf unit, side-by-side, pull-out drawers are provided at the front of the desk for storage.

The wheelchair-lift portion of the invention comprises a wheelchair platform upon which the wheelchair is rolled and securely positioned for vertical lifting. The platform is rotatably mounted upon a rectangular platen which attaches at opposite ends thereof to first and second, laterally spaced lifting mechanisms.

A slide assembly interconnects the lift assembly (comprising the platform, platen and lifting mechanisms) to the desk whereby the lift assembly slidingly depends in a horizontal direction (perpendicular to the direction of the wheelchair lifting mechanisms) from the desk thereby providing movement of the lift assembly from a first, stored position beneath the top surface and between the legs of the desk, to a second, extended position adjacent and spaced from the front of the desk. When the lift assembly is moved to the second, extended position, a person may roll their wheelchair onto the platform for lifting.

The lifting mechanisms are electrically actuated and appropriate switches are provided on the desk to effect vertical movement of the lift assembly from a fully lowered to a fully raised position which is approximately twenty inches from the floor although it is intended that the vertical lifting height of the platform be adjustable in accordance with personal preferences.

DETAILED DESCRIPTION

Figure 1:
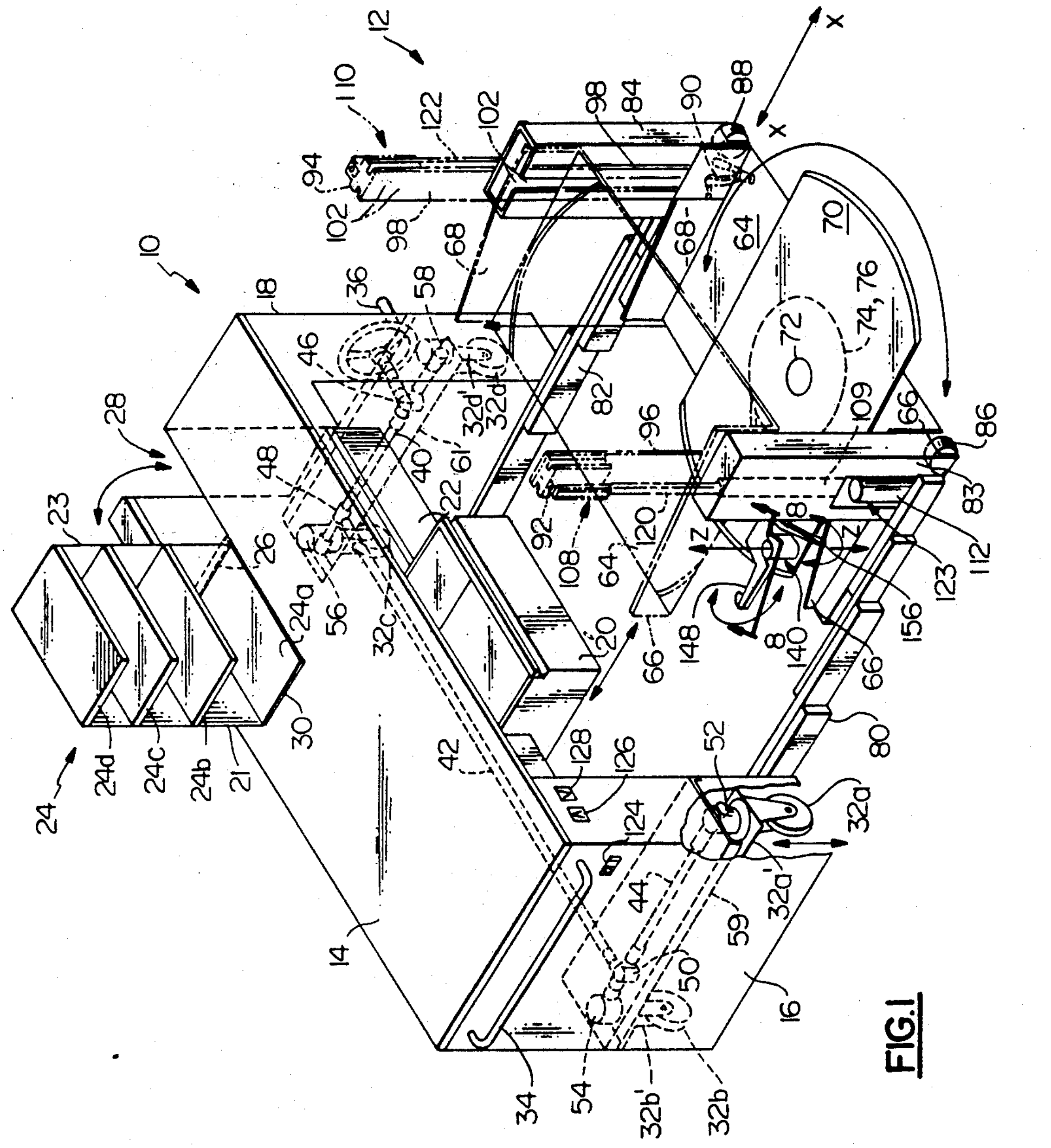
FIG. 1 is a perspective view of the combined desk and wheelchair lift showing the lift assembly in the extended position spaced from the desk. The lifting mechanisms and lift platform are shown both in the fully lowered (solid lines) and fully raised (dotted lines) positions. A portion of the desk is broken away to reveal a caster assembly with other portions of the caster assembly shown in dotted lines.

Referring now to the drawings, the invention comprises a combined desk and wheelchair lift designated generally by the reference numerals 10 and 12, respectively, as seen in FIG. 1. Desk 10 and wheelchair-lift 12 are designed especially for ophthalmic examinations as will be described more fully below although it will be readily apparent that desk 10 and lift 12 may be utilized by any wheelchair-seated person for many other purposes.

Discussing first the desk 10 portion of the invention, it is seen desk 10 is of generally rectangular configuration having a planar top surface 14 and left and right support legs 16 and 18 extending downwardly therefrom, respectively. A pair of front drawers 20 and 22 are slidingly mounted beneath top surface 14 between support legs 16 and 18, drawer 20 shown in the partially open position.

A stacked shelf unit 24 is comprised of four individual shelves 24*a–d* interconnected by walls 21 and 23 which are disposed at a 90° angle to each other. Shelf unit 24 is pivotally connected to top surface 14 of desk 10 by a hinge 26. It is seen best in FIG. 1 that top surface 14 and right support leg 18 include a generally rectangular cut-away forming a recess 28 in which shelf unit 24 may cooperatively fit when swung along the hinge axis to the closed, stored position seen in solid outline in FIGS. 3 and 4. In particular, bottom shelf 24*a* lies in covering relation to top surface 14 when in the open position seen in FIG. 1. When shelf unit 24 is swung to said closed, stored position in accordance with the directional arrow of FIG. 1, bottom shelf 24*a* lies co-planar with desk top surface 14, the edge 30 of shelf 24*a* opposite hinge 26 completing a rectangular perimeter with top surface 14 of desk 10.

Figure 2:
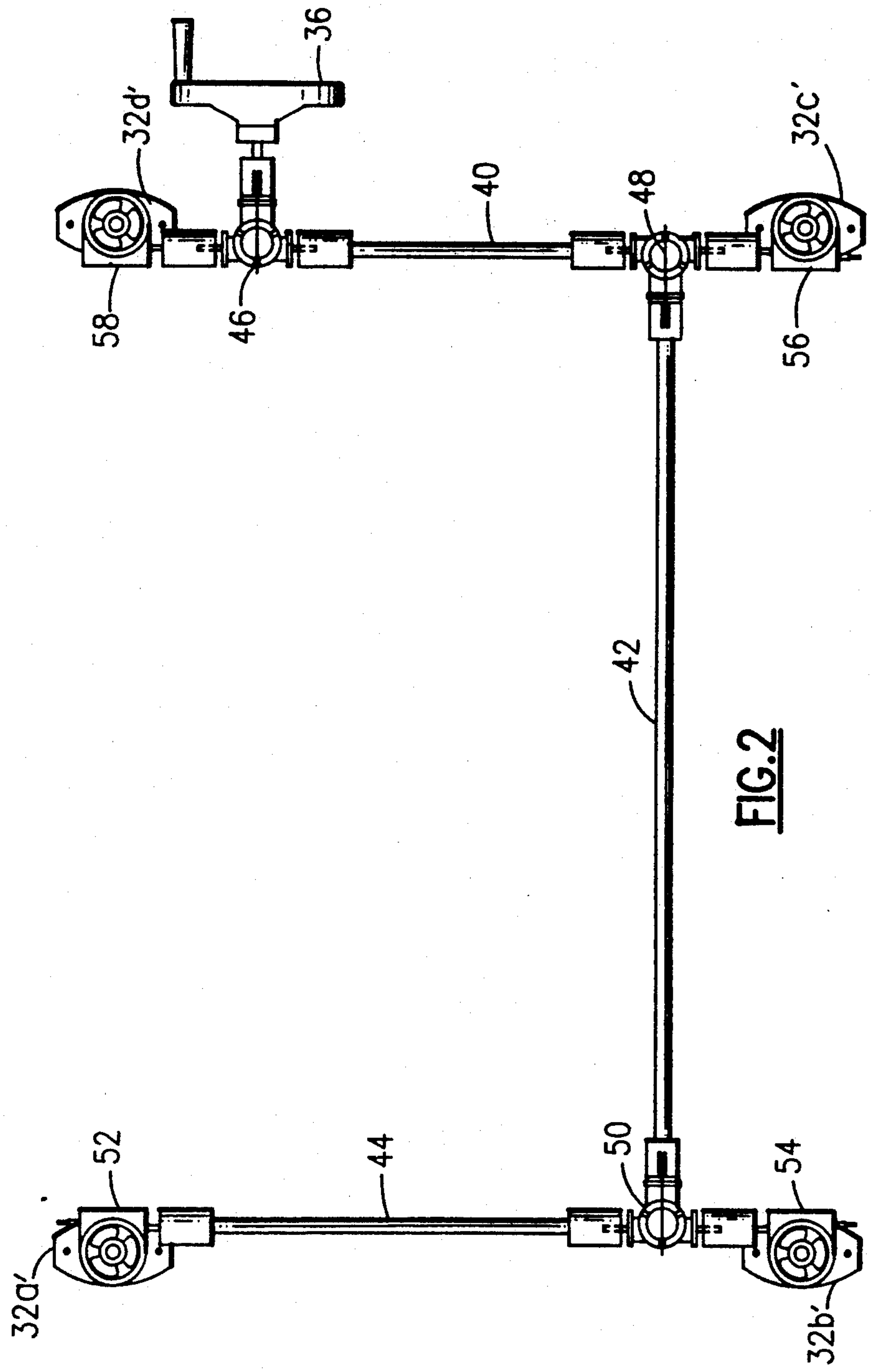
FIG. 2 is a top plan view of the caster assembly.
Figure 4:
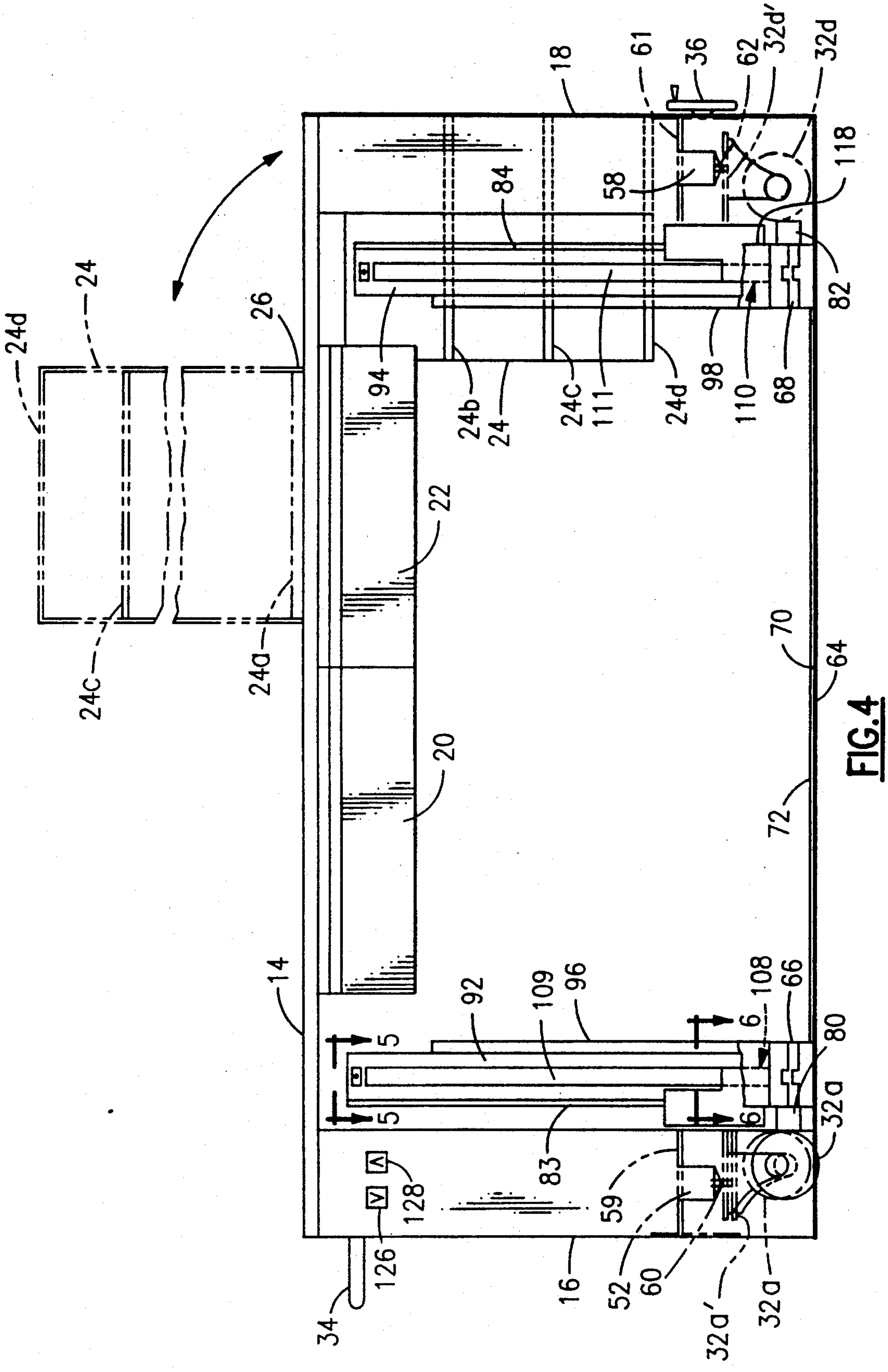
FIG. 4 is a front elevational view of the desk and wheelchair lift showing the wheelchair lift in the stored position and the desk shelf assembly in the raised position in dotted lines.

Desk 10 includes a retractable caster assembly comprising a set of four casters 32*a–d* mounted and disposed at the four corners of support legs 16 and 18, each interconnected to the other by linkages 40, 42 and 44 (FIG. 2). In the extended position, casters 32*a–d* provide mobility to desk 10 and lift 12 whereby a person may manually grasp handle 34 mounted to support leg 16 and push and/or pull desk 10 and lift 12 to any desired location. In the preferred embodiment, at least casters 32*a* and 32*b* are of the swivel type making desk 10 and lift 12 easily directed around corners. It is also understood that lift 12 would be moved to the stored position beneath desk top surface 14 as seen in FIG. 4 (in the manner to be described) when moving the entire unit upon casters 32*a–d*.

After desk 10 and lift 12 have been moved to the desired location, casters 32*a–d* may be selectively retracted relative to desk 10 whereby they assume a position above the bottom edge of support legs 16 and 18. The retracted position of casters 32*a–d* (caster 32*a* is seen in the retracted position in FIG. 1 and in upper dotted outline in FIG. 4) permit the bottom edges of support legs 16 and 18 to rest directly upon the floor providing secure positioning of desk 10 and lift 12.

Specifically, the caster retracting mechanism is actuated by a manually operable crank 36 extending through support leg 18 and connecting to linkage 40. Turning of crank 36 rotates linkage 40 which in turn imparts rotation to linkages 42 and 44 through mating bevel gears (not shown) housed in gear boxes 46, 48 and 50, respectively. Caster lifts 52, 54, 56 and 58 are anchored to support legs 16 and 18 by mounting brackets 59 and 61, respectively, each lift including a downwardly extending threaded rod lying in fixed position relative to desk 10. Two such rods 60 and 62 are seen in FIG. 4 and are threaded through apertures in caster yokes 32*a'* and 32*d'*, respectively, whereby rotation of each of the threaded rods (via bevel gears and linkages 40, 42 and 44) cause the caster yokes to ride up and down upon the rods thereby retracting and extending the associated casters, respectively.

Figure 3:
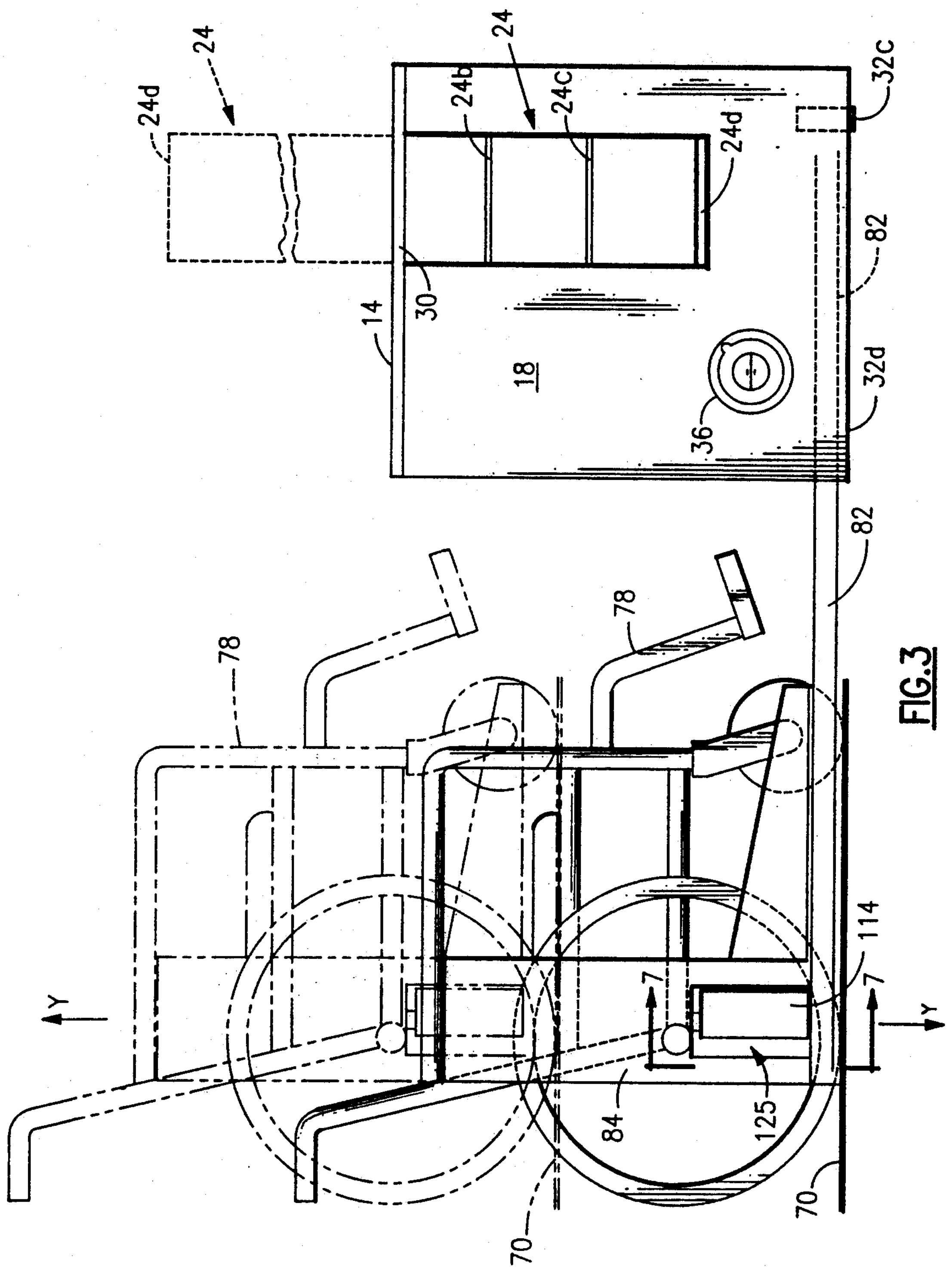
FIG. 3 is a side elevational view of the desk and wheelchair lift showing the lift assembly extended with a wheelchair positioned thereon for lifting from the lowered (solid lines) to the raised position (dotted outline). The desk shelf assembly is shown in both lowered (solid lines) and raised (dotted lines) positions also.
Figure 7:
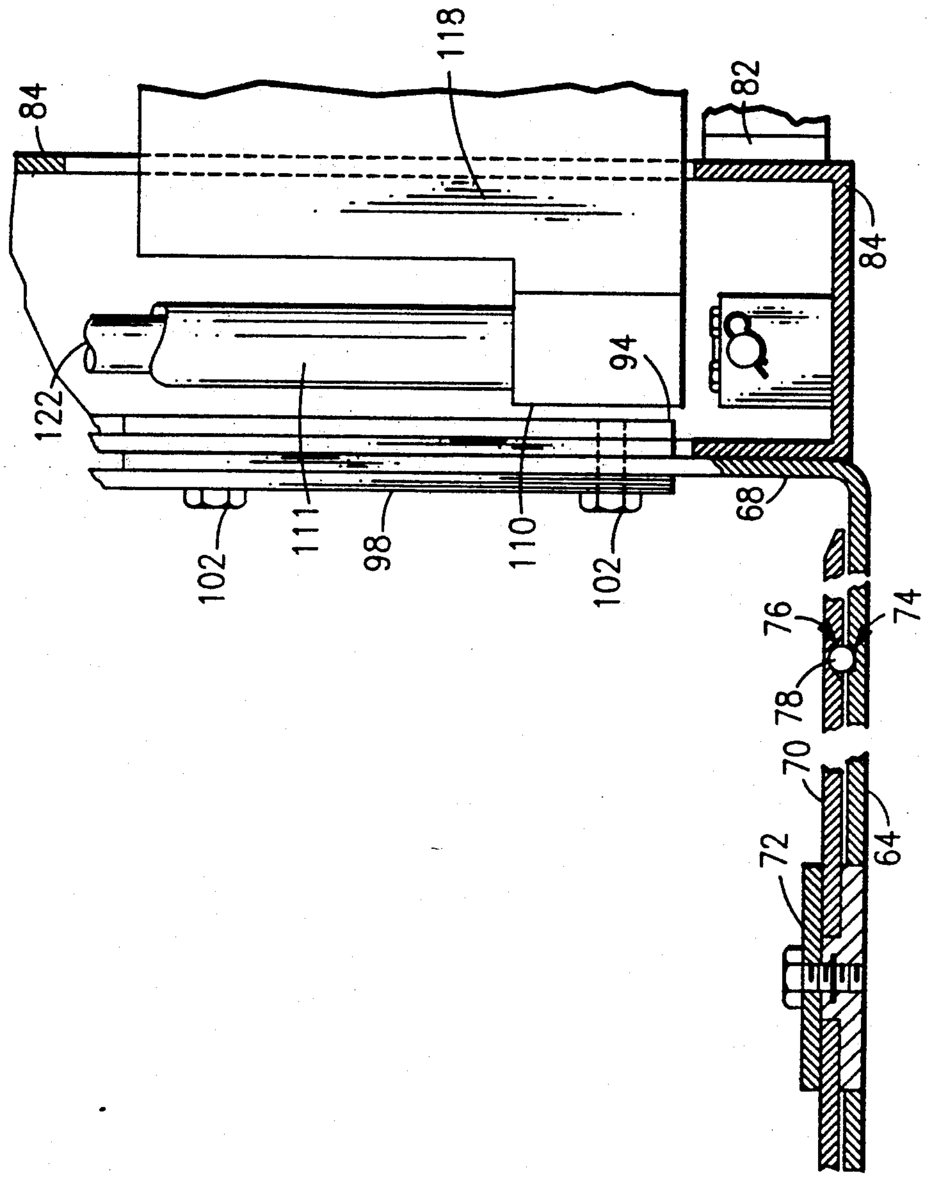
FIG. 7 is a cross-sectional view of the right lift assembly as taken generally along the line 7—7 in FIG. 3.

Turning attention now to lift assembly 12, it is seen in FIG. 1 that lift assembly 12 comprises a generally rectangular platen 64 movable between a fully lowered position seen in solid lines and a fully raised position seen in dotted lines (see also FIG. 3). Platen 64 includes upwardly extending side walls 66 and 68 which attach platen 64 to the lifting mechanisms to be described. A wheelchair platform 70 is rotatably mounted to platen 64 by bushing 72. As seen in the cross-sectional view of FIG. 7, the facing surfaces of platen 64 and platform 70 include aligned, annular grooves 74 and 76, respectively, with a plurality of ball bearings 77 disposed therein to decrease friction during rotation of platform 70 upon platen 64. Platform 70 is rotatable upon platen 64 through a full 360° angle in accordance with the large annular directional arrow seen in FIG. 1. Although platform 70 is positioned as seen in FIG. 1 when a wheelchair is rolled thereon or thereoff, a wheelchair with seated patient positioned on platform 70 may be rotated to face in a variety of directions as desired or required. It is presumed that most present-day wheelchairs, such as wheelchair 78 seen in FIG. 3, are equipped with braking mechanisms which permit the wheelchair to be braked once positioned on platform 70.

As aforementioned, lift assembly 12 may be moved along a horizontal axis x—x (FIG. 1) between an "extended" position seen in FIGS. 1 and 3 with platform 70 exposed and ready for positioning wheelchair 78 thereon, and a "stored" position beneath desk top surface 14 and between support legs 16 and 18 as seen in FIG. 4. A plurality of linking slider extensions 80, 82 of the roller/track type are provided on opposite sides of platen 64, attaching to support legs 16 and 18 at first ends thereof and to outer surfaces of lift housings 83 and 84 at second, opposite ends thereof, respectively. Casters 86 and 88 are provided at forward, bottom ends of lift housings 83 and 84, respectively, to facilitate moving lift assembly 12 to and from the extended and stored positions.

Reference is now made to the lifting mechanisms which permit platen 64 and platform 70 to be lowered and raised along vertical axis y—y (FIG. 3) when lift assembly 12 is in said extended position. The ensuing description at times will refer particularly to a single lift mechanism; however, it is understood that the lift mechanisms within lift housings 83 and 84 are identical.

Upwardly extending side walls 66 and 68 of platen 64 are fixedly attached to follow slides 92 and 94 by elongated securing straps 96, 98 and bolts 100, 102 extending laterally therethrough, respectively. Referring to FIG.

5, it is seen that the upper end of follow slide 92 includes a pair of shoulders 104, 106 which attach to an electric lift mechanism designated generally by numeral 108 which is centrally and longitudinally positioned within lift housing 83. Lift mechanisms 108, 110 may be purchased through Raco International, Inc. of Bethel Park, Pa. by Model No. LA 30S. Electric lift mechanisms 108, 110 are operable via motors 112, 114 and worm and bevel gears housed within gear boxes 116, 118 to extend and retract elongated shafts 120, 122 longitudinally extending through and movable within cylinders 109, 111, respectively. Motors 112, 114 extend through openings 123, 125 formed in the outer walls of housings 83, 84 and are actuable by switches 124, 126 and 128 mounted on support wall 16 (FIG. 1) which are the on/off, lift up and lift down switches, respectively. Although not shown, a terminal plug is provided to plug into a conventional 110 V AC outlet to supply electricity to lift mechanisms 108, 110.

Figure 5:
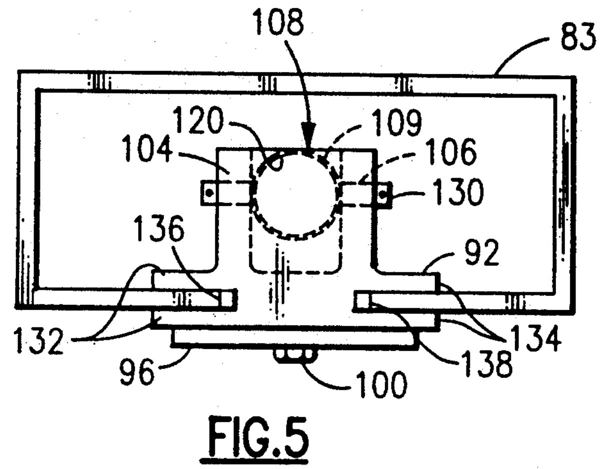
FIG. 5 is a cross-sectional view of the left lift assembly as taken generally along the line 5—5 in FIG. 4.
Figure 6:
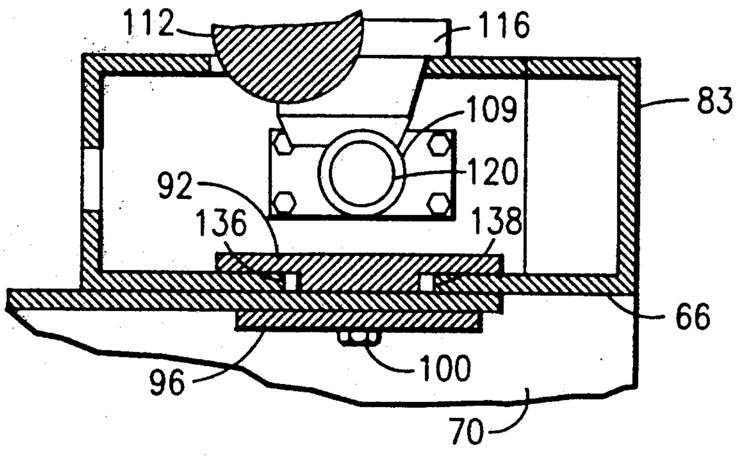
FIG. 6 is a cross-sectional view of the left lift assembly as taken generally along the line 6—6 in FIG. 5.

Referring back to FIG. 5, shoulders 104, 106 attach follow slide 92 to shaft 120 by a mounting bracket 130. A pair of diametrically opposed, spaced, double fingers 132 and 134 engage co-planar, spaced edges 136 and 138 which extend the full length of housing 83 to guide follow slide 92 (including attached strap 96 and platen side wall 66) longitudinally along lift housing 83 as shaft 120 is raised and lowered therein by selective actuation of motor 112 via switches 124, 126 and 128.

Figure 8:
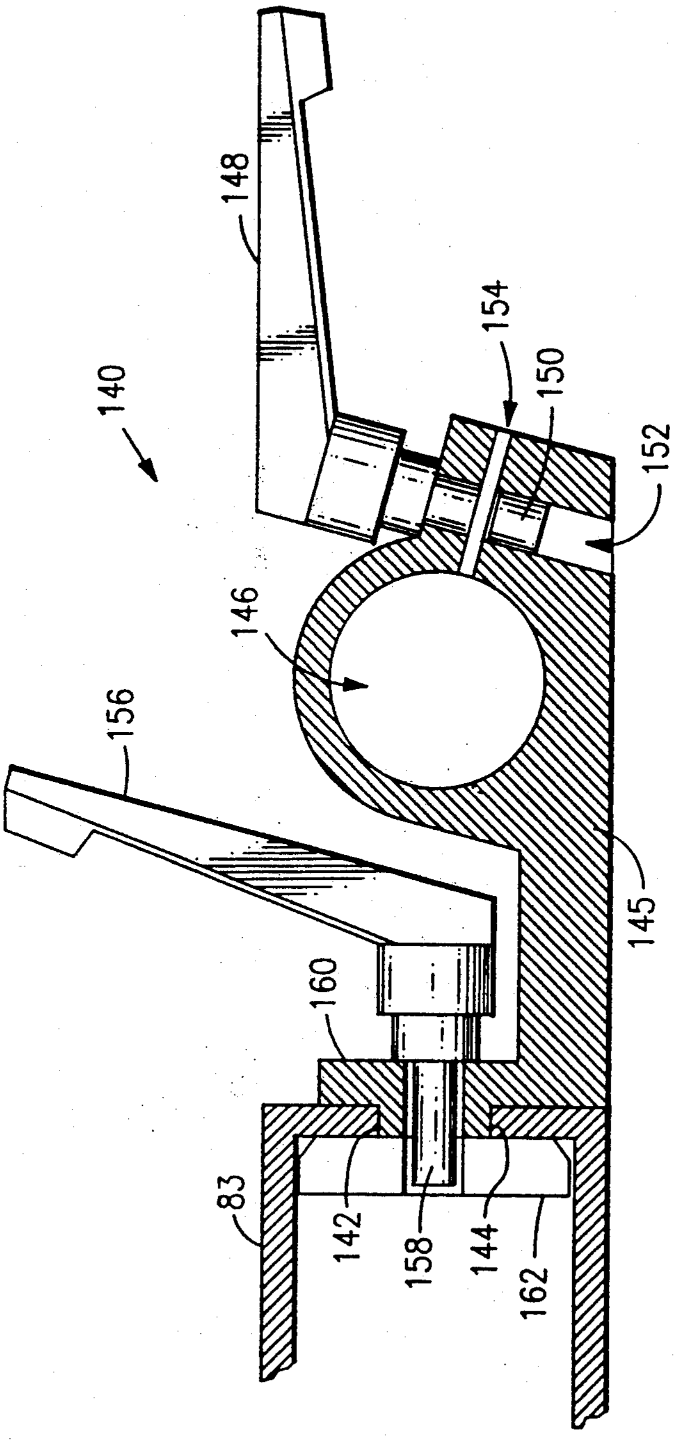
FIG. 8 is a cross-sectional view of the clamp assembly as taken generally along the line 8—8 in FIG. 1.

Referring to FIGS. 1 and 8, a clamp assembly denoted generally by the reference numeral 140 is adjustably and slidingly attached within a longitudinal slot formed in the side of lift housing 83 facing desk 10. As seen in the cross-sectional view of FIG. 8, co-planar, spaced edges 142 and 144 define the longitudinal slot of lift housing 83 wherethrough clamp assembly 140 extends to attach to housing 83. In particular, clamp assembly 140 includes a main body portion 145 with a circular opening 146 wherethrough a pole (not shown) is telescopically positioned to lie along axis z—z (FIG. 1). A first handle 148 is operable to adjust the diameter of opening 146 about the pole such that the pole may be moved up and down along axis z—z as desired with the surfaces of body portion 145 defining opening 146 frictionally engaging and clamping the pole at the desired height. Handle 148 operates by rotating a threaded rod 150 extending therefrom into a threaded bore 152 formed in body portion 145. As seen, body portion 145 includes a slot 154 extending from the distal end of body portion 145 to opening 146. With threaded rod 150 extending across slot 154, handle 148 is operable to open and close slot 154 upon itself which hence increases and decreases the diameter of opening 146, respectively.

In a similar manner, a second handle 156 is operable to rotate a threaded rod 158 extending therefrom, through integral plate 160 of body portion 145, and into a threaded bore in nut 162 located inside lift housing 83. Handle 156 is thus operable to frictionally engage the portions of housing 83 adjacent edges 142 and 144 between nut 162 and plate 160 allowing clamp assembly 140 to be adjustably positioned at varied heights along housing 83.

The aforementioned pole which is telescopically positioned in opening 146 provides a medium to which may be mounted a variety of ophthalmic examination equipment such as a slitlamp, refractor or keratometer. The pole and equipment are not shown in the drawings since they are conventional apparatus with the means rotatably and removably mounting the equipment to the pole being well known in the art as can be seen in virtually every ophthalmic examination room. Instead of the same pole and equipment being mounted adjacent the conventional ophthalmic examination chair, they are mounted to clamp assembly 140 adjacent platform 70 in the present invention. The aforementioned adjustability features which handles 148 and 156 provide clamp assembly 140, permit the examination/treatment equipment to be positioned directly adjacent the head of a patient seated in wheelchair 78 as needed.

It is intended that platform 70 be rotated 90° in a counterclockwise direction from the position seen in FIG. 1 during use of ophthalmic equipment attached to clamp assembly 140. Also, the distance between desk 10 and lift assembly 12 when lift assembly 12 is in the fully extended position is such that the examiner may position themself between the seated patient on platform 70 and desk 10 as needed. A clamp 90 is provided to engage and clamp a curved edge of platform 70 during examination/treatment of a wheelchair-seated patient.

There is thus provided a novel and unique desk and wheelchair lift combination for facilitating ophthalmic or other medical-surgical examination/treatment of wheelchair-seated patients. Although the foregoing description has emphasized the suitability of the invention for ophthalmic examinations, it should be evident that desk 10 and lift 12 may be used for any number of a variety of purposes in a variety of settings. For example, a wheelchair-seated person may find desk 10 and lift 12 very useful in the home as a work/hobby desk. In this instance, control of lift 12 may be made remote such that the wheelchair-seated person may operate lift 12 by him/herself to position themselves with horizontal, vertical and rotational freedom.

While the foregoing has described the invention with particular reference to a preferred embodiment thereof, it should be apparent to those skilled in the art that changes and modifications may be made thereto without departing from the full spirit and scope of the invention which are defined by the claims which follow.

What is claimed is:

1. A combination desk and wheelchair-lift assembly comprising:

a) a desk having a top, planar surface with at least two support legs extending therefrom adapted to position and support said top surface a predetermined distance above a substantially planar floor surface; and b) a wheelchair-lift assembly including a wheelchair platform attached to and depending from said desk, said wheelchair-lift assembly selectively movable in a first, horizontal direction between a stored position wherein said wheelchair-lift assembly is positioned between said desk top surface and said floor surface, and an extended position wherein said wheelchair-lift assembly is spaced a predetermined distance from said desk, said wheelchair-lift assembly selectively further movable in a second, vertical direction with respect to said desk when in said extended position between a fully lowered and fully raised position whereby a wheelchair and person seated in said wheelchair may roll onto and off of said platform when said wheelchair-lift assembly is in said extended, fully lowered position and be lifted in said vertical direction relative to said desk when said wheelchair is rolled onto said platform and said lift assembly is moved to said second, fully raised position, said platform always lying in planes parallel to said desk top, planar surface as said lift assembly is moved between said fully raised and lowered positions.

2. The invention according to claim 1 wherein said wheelchair-lift assembly comprises:

a) first and second, laterally spaced lift mechanisms, said platform positioned between and attached to said lift mechanisms and movable therewith; and b) means attached to said desk and said lift mechanisms providing said selective movement of said lift assembly between said stored and extended positions.

3. The invention according to claim 2 wherein said wheelchair-lift assembly further comprises a platen extending between and attached to said first and second lift mechanisms, said platform being rotatably mounted in covering relation to said platen.

4. The invention according to claim 3 wherein said first and second lift mechanisms each comprise a cylinder and a telescoping shaft movable within said cylinder wherein said cylinders are stationary and said platen is attached to and movable with said shafts with respect to said cylinders, and further comprising actuating means moving said shafts and platen between said fully raised and lowered positions.

5. The invention according to claim 4 wherein said actuating means is an electric motor.

6. The invention according to claim 5 and further comprising first and second, elongated housings wherein said first and second lift mechanisms are positioned for operation.

7. The invention according to claim 6 wherein said means providing selective movement of said lift assembly between said stored and extended positions comprises a plurality of linking slider extension members.

8. The invention according to claim 6 wherein said first and second housing include respective first and second longitudinal slots and said first and second lift mechanisms further include respective first and second follow slides positioned for sliding, vertical movement within said first and second longitudinal slots, respectively, with a first portion of each of said follow slides attached to a respective shaft and a second portion of each of said follow slides attached to said platen.

9. The invention according to claim 8 wherein said first and second lift mechanisms further include respective first and second elongated straps attaching said plate to said first and second follow slides, respectively.

10. The invention according to claim 1 and further comprising means making said desk and wheelchair lift combination mobile.

11. The invention according to claim 10 wherein said mobile means comprise first and second caster assemblies respectively attached to said legs.

12. The invention according to claim 11 wherein said first and second caster assemblies comprise respective first and second casters and caster lift mechanisms and further including means selectively actuating each of said caster lift mechanisms to move said casters between an extended, floor engaging position wherein said legs are spaced above said floor surface, and a retracted position wherein said legs engage said floor surface and said casters are positioned adjacent a respective one of said legs.

13. The invention according to claim 12 wherein said first and second caster lift mechanisms comprise respective:

a) first and second rotatable, threaded rods fixedly positioned relative to said desk; and b) first and second caster yokes respectively attached to said first and second casters and threadedly engaged with said first and second threaded rods for selective movement of said caster yokes in response to rotation of said threaded rods to move said casters between said extended and retracted positions.

14. The invention according to claim 13 wherein said means selectively actuating each of said caster lift mechanisms comprises:

a) a linkage extending between and attaching to each of said threaded rods of each of said caster lift mechanisms;

b) a hand-crank mounted to one of said legs and attached to said linkage;

c) means transmitting torque from said hand-crank to said linkage; and d) means transmitting torque from said linkage to said threaded rods.

15. The invention according to claim 14 wherein said torque transmitting means comprise a plurality of mating bevel gears 16. The invention according to claim 1 wherein said desk includes a stacked shelf assembly pivotally connected along an edge thereof to said desk top surface whereby said shelf assembly may be pivoted between a stored position with a surface of said shelf assembly lying co-planar with said desk top surface and the remaining portion of said shelf assembly lying below said top surface in the same direction as said legs extend, and an open position where said shelf assembly surface lies in covering relation to said desk top surface and said remaining portion extends upwardly therefrom in a direction opposite to said same direction.

17. The invention according to claim 1 wherein said desk includes a stacked shelf assembly connected thereto, said shelf assembly movable with respect to said desk between a stored position with a first surface of said shelf assembly lying co-planar to said desk top surface and the remaining portion of said shelf assembly lying below said top surface in the same direction as said legs extend, and an open position where a second shelf assembly surface located opposite said first surface lies co-planar to said desk top surface with said remaining portion extending upwardly therefrom in a direction opposite to said same direction.

* * * * *